US011769583B2

(12) United States Patent
Stranjak (10) Patent No.: US 11,769,583 B2
(45) Date of Patent: Sep. 26, 2023

(54) SYSTEMS AND METHODS FOR GENERATING A RESULT IMAGE (71) Applicant: Siemens Healthcare GmbH, Erlangen (DE)

(72) Inventor: Armin Stranjak, Uttenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 218 days.

(21) Appl. No.: 16/825,305

(22) Filed: Mar. 20, 2020

(65) Prior Publication Data

US 2020/0303061 A1   Sep. 24, 2020

(30) Foreign Application Priority Data

Mar. 21, 2019   (EP) .................... 19164235

(51) Int. Cl.
*G16H 30/20* (2018.01)
*G16H 30/40* (2018.01)
*G01R 33/54* (2006.01)
*G06T 7/00* (2017.01)

(52) U.S. Cl.
CPC .......... *G16H 30/20* (2018.01); *G01R 33/54* (2013.01); *G06T 7/0014* (2013.01); *G16H 30/40* (2018.01); *G06T 2207/10088* (2013.01); *G06T 2207/20212* (2013.01)

(58) Field of Classification Search
CPC ........ G16H 30/20; G16H 30/40; G01R 33/54; G06T 7/0012; G06T 7/0014; G06T 2207/10088; G06T 2207/20212; G06T 2207/20216; G06T 2207/2021; G06F 3/0611; G06F 3/0613; G06F 3/0614; G06F 3/0617; G06F 3/0619
See application file for complete search history.

(56) References Cited

U.S. PATENT DOCUMENTS 6,192,432 B1    2/2001   Slivka et al.
2007/0266197 A1* 11/2007 Neyama ............... G06F 3/0613
                                         710/310

(Continued)

OTHER PUBLICATIONS

Wikipedia: "In-memory data base"; pp. 1-4; Feb. 28, 2019; Retrieved from the Internet: URL:https://en.wikipedia.org/w/index.php?title=Inmemory_database&oldid=885569816.

(Continued)

*Primary Examiner* — Vincent Rudolph
*Assistant Examiner* — Timothy Choi
(74) *Attorney, Agent, or Firm* — Banner & Witcoff Ltd.

(57) ABSTRACT

In a method for generating at least one medical result image from a plurality of single-frame images, the plurality of single-frame images referring to a medical image acquisition procedure conducted with a medical imaging system, at least one first parameter representative for the medical image acquisition procedure is acquired, and the at least one first parameter is evaluated to generate an evaluation result. Based on the evaluation result, it is decided whether to: (i) combine at least partially the plurality of single-frame images to generate the result image before permanently storing the result image, or (ii) permanently store the plurality of single-frame images before combining them to generate the result image.

20 Claims, 4 Drawing Sheets (56) References Cited

U.S. PATENT DOCUMENTS

| | | | |
|---|---|---|---|
| 2007/0280560 A1* | 12/2007 | Dennison | G16H 30/40 |
| | | | 382/305 |
| 2008/0052112 A1* | 2/2008 | Zahlmann | G16H 10/20 |
| | | | 705/2 |
| 2013/0039549 A1* | 2/2013 | Muller | G01R 33/5608 |
| | | | 382/128 |
| 2016/0232691 A1* | 8/2016 | Nishii | G06T 11/008 |
| 2018/0239867 A1* | 8/2018 | Kopylov | G06T 3/4092 |

OTHER PUBLICATIONS

European Search Report dated Sep. 10, 2019, Application No. 19164235.4.

* cited by examiner

SYSTEMS AND METHODS FOR GENERATING A RESULT IMAGE

CROSS REFERENCE TO RELATED APPLICATIONS

This patent application claims priority to European Patent Application No. 19164235.4, filed Mar. 21, 2019, which is incorporated herein by reference in its entirety.

BACKGROUND

Field

The present disclosure relates to systems and methods for generating at least one medical result image.

Related Art

Nowadays, medical images are acquired with a medical imaging modality like a CT (Computed Tomography) system or an MR (Magnetic Resonance) system and reconstructed sequentially, i.e. one by one.

Traditionally, most of recent medical imaging applications create single-frame DICOM (Digital Imaging and Communications in Medicine) images as result images and store them permanently as soon as they become available after the reconstruction process. This approach however is considered inefficient in terms of data storage requirements, as thousands of images from the same acquisition or measurement would repeatedly store the same data, e.g. data like patient name, age or sex, like protocol parameters applied for image acquisition or other study details usually included in the DICOM header. This limits storage availability.

To avoid this problem, storage of a multi-frame DICOM image can be chosen for the result image. Accordingly, a plurality of individual images or image frames is stored collectively in one coherent image, e.g. as a volume image stack or a time series. A multi-frame image is thus characterized in that it contains only one DICOM header, which refers to all individual images within the multi-frame image. Typical example for a medical multi-frame image is a multi-frame MR image according to DICOM standard, which represents spatial volumes (e.g. neurological images in functional MR applications) or a time series (e.g. a cardio time series of an MR heart scan). Here, thousands of individual images are created representing either hundreds of different volumes or a time series within a short period of time (e.g. several minutes) each series element representing the same volume/slice at a slightly different time point.

However, storing of coherent multi-frame images is also challenging for the following reason:

If individual images need to be combined into multi-frame (or multi-stack) image in order to be made available for further user analysis as soon as possible, these images need to be combined into temporary fast-speed storage device (typically RAM memory) before being permanently stored on an external storage device (e.g. an external hard drive or solid state drive). Fast availability is thus possible. However, in case of power loss or insufficient memory during image processing, image data or images only stored temporarily may be lost. The effort spent to reconstruct these individual DICOM images from corresponding measured raw data would be lost and would require additional reconstruction time.

On the other hand, if individual images/image frames need to be secured first from loss by storing them one by one, the overall duration until they are available for the user will be jeopardized, as the securing implies time-consuming reload of the images into the RAM memory before they can be coherently combined into the DICOM multi-frame image. Thus, risk of data loss is minimized, but availability time is extended.

Except for few predefined cases, fast availability of multi-frame images has higher priority and thus 'first-combine and permanently store the multi-frame image' is the established method of choice, which at the same time neglects the risk to lose individual images, even in cases where availability time is usually not critical.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

It is thus an object of the present disclosure to provide alternative means and/or methods which allow processing and/or storing of medical images with the enablement of choice between applying fast but risky processing, or slow but safe processing for generation of a DICOM multi-frame image.

The plurality of single-frame images refers to a medical image acquisition procedure conducted with a medical imaging system. The object is further solved by corresponding computer, medical imaging system, computer-program product and computer-readable storage medium according to aspects of the present disclosure.

A first aspect of the present disclosure is directed to a method for generating at least one medical result image from a plurality of single-frame images, wherein the plurality of single-frame images refers to a medical image acquisition procedure conducted with a medical imaging system.

The claimed plurality of single-frame images corresponds to at least two, preferably numerous medical images. One single-frame image preferably corresponds to a medical image according to DICOM standard, wherein the single-frame image typically has two spatial dimensions. The plurality of single-frame images all refer to a medical image acquisition procedure. With other words, the plurality of single-frame images is acquired in the course of the same medical image acquisition procedure, i.e. the same medical radiological examination. Depending on the image acquisition technique and on the applied imaging protocol, the plurality of single-frame images may be acquired at least partially at the same time point or at different time points. One single-frame image out of the plurality of single-frame images may thus correspond to a two-dimensional slice image out of a three-dimensional volume according to the field of view (FOV) of the medical imaging system. Alternatively, one single-frame image out of the plurality of single-frame images may correspond to a two-dimensional slice image representing the imaged body region at the respective acquisition time point within a time series, wherein all single-frame images refer to the same body region. Alternatively, the plurality may refer to different body regions and different points in time.

The claimed result image corresponds to a coherent DICOM multi-frame image representing either a three-dimensional volume data set or a three-dimensional time series data set comprising two spatial and a time dimension. Advantage of the multi-frame image is the lack of redundancy as regards meta-information of the single-frame images, for example header data referring to patient or imaging protocol specific data like patient name, patient age or imaging parameters applied to the medical imaging system during image acquisition.

The method comprises a plurality of steps.

A first step is directed to acquiring at least one first parameter representative for the medical image acquisition procedure. A further step is directed to evaluating the at least one first parameter. A further step is directed to deciding to
i. combine at least partially the plurality of single-frame images to generate the result image before permanently storing the result image (process first), or
ii. permanently store the plurality of single-frame images before combining them to generate the result image (store first).

According to the disclosure, this decision is based on the result of the evaluation of the at least one parameter.

The first alternative mentioned corresponds to a 'process-first' approach. According to this approach the single-frame images already reconstructed from the raw data measured during medical imaging procedure are stored only temporarily and instantaneously processed into a result image within the image processing pipeline of the medical imaging system. Only the result image is stored permanently afterwards.

The second alternative mentioned corresponds to a 'store-first' approach and comprises an initial permanent storage step for each of the plurality of single-frame images. Only afterwards the single-frame images are read out again and combined into the result image.

While the second alternative is more time-consuming, but safer as regards potential loss of single-frame images, the first alternative is remarkably fast, but bears the risk of losing single-frame images.

The inventor now realized that depending on the image acquisition procedure either the first or the second one of the alternatives is better suited for further processing the single-frame images, as the image acquisition procedure is indicative of the referral or the initial medical question the medical images shall support to answer. Accordingly, at least one parameter indicative or representative of the image acquisition procedure is acquired and evaluated to find out, which alternative is best suited for the plurality of single-frame images. Suitability may for example depend on how fast the multi-frame images need to be available for a user, e.g. for emergency medicine time is a crucial factor.

Evaluation may especially comprise comparing the parameter to a predefined threshold, wherein the threshold value may be an automatically or manually predefined value. The threshold value may likewise correspond to or depend on the image acquisition procedure.

According to another embodiment of the disclosure a plurality of first parameters is acquired and evaluated. In this embodiment, each of the plurality of first parameters may be evaluated individually without taking into account the other first parameters. In this case, each first parameter may be compared to its corresponding threshold value. Alternatively, the evaluation may further comprise to establish a correlation between different parameters, in case more than one parameter is acquired and considered. In this case, their correlation and/or common impact on the imaging procedure may be evaluated, too. Especially, a plurality of first parameters may have an antagonistic impact on the decision which alternative to apply.

The inventive method may comprise the generation of only one or a plurality, i.e. at least two or more result images. Accordingly, the at least one result image may be generated by combining all of the plurality of single-frame images or only a part or a sub-group of the plurality of single-frame images. Accordingly, in case of more than one result image is generated each result image is especially generated by combining different sub-groups of the plurality of single-frame images.

The inventive method may comprise that more than one method step is conducted at least partially in parallel, i.e. at the same time, especially in case of generation of more than one result image.

According to an embodiment of the disclosure the second alternative, i.e. the 'store-first' approach, comprises to permanently store a sub-group of the plurality of single-frame images before combining the sub-group of the plurality of single-frame images to generate the result image. With other words, according to this embodiment, all single-frame images which are supposed to contribute to one result image out of a plurality of result images, are permanently stored before generating the corresponding result image. This embodiment represents a 'hybrid' approach, as it minimizes the risk to lose image data with justifiable time delay.

According to this embodiment, permanent storage of another sub-group of single-frame images supposed to contribute to a consecutive result image may take place contemporaneously with the combination of the sub-group of single-frame images to generate the previous result image.

According to another embodiment of the disclosure, the first alternative ('process-first') is chosen, if the at least one first parameter is below a predefined threshold. With other words, in this embodiment the at least one parameter falls below or is smaller than a threshold value. Then, the method comprises the step of transferring the plurality of single-frame images to a temporal storage and processor. The single-frame images may be transferred e.g. from an image generator like e.g. an image reconstruction processor to the temporal storage and processor. These components may be integral parts of the medical imaging system. A further step is to generate the medical result image by combining the plurality of single-frame images by the temporal storage and processor. Another step is to transfer the medical result image to a permanent memory storage unit (i.e. permanent memory). Another step is to permanently store the result image in the permanent memory storage unit.

According to this embodiment, processing time is a critical criterion. This alternative is thus chosen, when the at least one result image needs to be available fast. This embodiment avoids the time consuming and thus delaying step of permanently storing each individual single-frame image. Instead, only the at least one result image is permanently stored. By doing so, not only the time needed to permanently store the single-frame images can be saved, but also the time needed to read out again and transfer the single-frame images from the permanent memory storage unit to the temporal storage and processor.

According to another embodiment of the disclosure, the second alternative ('store-first') is chosen, if the at least one first parameter is above a predefined threshold. With other words, in this embodiment, the at least one parameter exceeds a threshold value. Then, the method comprises the step of transferring the plurality of single-frame images to a permanent memory storage unit. This step may comprise a transfer of the plurality of single-frame images from an image reconstruction processor to the permanent memory storage unit via the temporal storage and processor. A further step is to permanently store the plurality of single-frame images in the permanent memory storage unit. Another step is to transfer the plurality of single-frame images (back) to the temporal storage and processor. A further step is to generate the medical result image by combining the plurality of single-frame images by the temporal storage and processor. A further step is to transfer the medical result image to a permanent memory storage unit. A further step is to permanently store the result image in the permanent memory storage unit.

According to this embodiment the safety for the single-frame images has highest priority. Accordingly, they are stored first. This implies additional time delay due to repeatedly read out and transfer efforts.

According to another embodiment of the disclosure the at least one first parameter is a protocol parameter characterizing the imaging protocol applied for the medical image acquisition procedure. The imaging protocol typically defines the type or kind of image acquisition, which is to be carried through for the patient in question. The imaging protocol is typically specific for imaging of a desired body region or organ or tissue type and/or may account for other anatomical features of a patient, e.g. obesity or the like. The imaging protocol may for example define the voltage or trajectory of an X-ray radiation source for a computed tomography imaging system or a certain pulse sequence for a magnetic resonance imaging system as a protocol parameter. The imaging protocol may likewise define a total number of single-frame and/or result images which need to be acquired.

According to an exemplary embodiment of the disclosure, the at least one first parameter is one of the following group of first parameters:
  total number of single-frame images acquired for the medical image acquisition procedure,
  total number of result images, i.e. multi-frame images acquired for the medical image acquisition procedure,
  number of single-frame images of one of a plurality of multi-frame images acquired for the medical image acquisition procedure, and
  size of one of at least one of the plurality of single-frame images.

The total number of result images to be acquired represents the total number of measurements conducted in the course of the image acquisition procedure, e.g. the image acquisition for a plurality of sub-volumes or the like. The number of single-frame images of one of a plurality of multi-frame images acquired for the medical image acquisition procedure defines the number of single frames which contribute to an individual measurement of the image acquisition procedure. Number of single frames per result image may differ from corresponding measurement to measurement. The size of a single-frame image is defined by the number of image elements, i.e. pixels in the two spatial dimensions.

It is especially advantageous to consider at least one, preferably more than one of the mentioned parameters, as all of them have direct impact on the time needed to store and/or process the medical images and thus on the overall duration of the inventive method.

According to another embodiment of the disclosure at least one second parameter is acquired and evaluated, wherein the second parameter is indicative of the storage behavior of at least one of the temporal and/or permanent storage and processors. Not only the size and/or total number of medical images which need to be processed and stored may impact the decision which processing alternative is best suited for a certain image acquisition procedure, but also the capacity, e.g. the read out velocity of the permanent memory storage unit or the velocity of the transfer/communication channels or interfaces available in the medical imaging system, and/or the behavior of the permanent storage and temporal storage and processors may do so. Accordingly, a further, i.e. a second parameter may be evaluated, e.g. compared to a predefined threshold value or correlated to at least one of the at least one first parameter.

Another aspect of the present disclosure is directed to a computer for generating at least one medical result image from a plurality of single-frame images, wherein the plurality of single-frame images refers to a medical image acquisition procedure conducted with a medical imaging system. In an exemplary embodiment, the computer includes:
  an evaluator configured to acquire and evaluate at least one first parameter representative for the medical image acquisition procedure,
  a temporal storage and processor configured to temporarily store the plurality of single-frame images and to combine at least partially the plurality of single-frame images to generate the at least one medical result image, and
  a permanent memory storage unit configured to permanently store either the plurality of single-frame images and/or the at least one result image.

According to an embodiment of the disclosure the computer is configured to implement the inventive method.

The computer may be configured to particularly carry out the step of generating the at least one medical result image by combining at least partially the plurality of single-frame images according to one of the above mentioned alternatives. The computer may likewise be arranged to carry out all the steps of the inventive method for an individual medical imaging system. The computer may further be configured to carry out the method for several medical imaging apparatuses in a hospital, a medical site or the like.

The computer can be realized as a data processing system or as a part of a data processing system. Such a data processing system can, for example, comprise a cloud-computing system, a computer network, a computer, a tablet computer, a smartphone or the like. The computer can comprise hardware and/or software. The hardware can be, for example, a processor system, a memory system and combinations thereof. The hardware can be configurable by the software and/or be operable by the software. Generally, all units, sub-units or modules may be at least temporarily in data exchange with each other, e.g. via network connection or respective interfaces. Furthermore, the evaluator may be further connected to a controller of the medical imaging system to gather the at least one first parameter. The evaluator may especially communicate with the temporal storage and processor and the permanent memory storage unit to gather the at least one second parameter. Consequently, individual components may be located apart from each other, especially the permanent memory storage unit may be located apart from the remaining components of the computer, e.g. in the cloud or as part of a regional server.

The temporal storage and processor may be implemented as tangible or non-transitory computer-readable storage medium, such as random access memory (RAM). The permanent memory storage unit may be implemented as a permanent mass storage device (such as a disk drive) or a solid state device.

The temporal storage and processor as well as the permanent memory storage unit preferably correspond to a combination of memory and processor system. The permanent memory storage unit may correspond to a PACS (Picture Archiving and Communication System) for permanent image storage typically further providing numerous retrieval and viewing options. The temporal storage and processor may preferably correspond to a fast speed memory, e.g. a random access memory (RAM).

Another aspect of the present disclosure is directed to a medical imaging system for generating at least one medical result image from a plurality of single-frame images, wherein the plurality of single-frame images refers to a medical image acquisition procedure conducted with the same. The medical imaging system or medical imaging apparatus comprises an inventive computer. Preferably, the computer is at least partially physically integrated into the medical imaging system. Alternatively, the computer can be located physically separated from the medical imaging system. A medical imaging system is an imaging apparatus for medical purposes. A medical imaging apparatus in particular may relate to imaging using optical electromagnetic radiation and/or X-Ray radiation. In particular, a medical imaging apparatus may be a C-arm x-ray apparatus typically used for acquiring angiography and/or fluoroscopy images, a computed tomography imaging apparatus, an X-ray imaging apparatus, a positron emission tomography (PET) imaging apparatus and/or an ultrasound imaging apparatus. Most preferably, the medical imaging system is a magnetic resonance imaging system.

Another aspect of the present disclosure is directed to a computer program comprising program elements which induce a computer to perform the steps of the inventive method, when the program elements are loaded into a memory of the computer.

Another aspect of the present disclosure is directed to a computer-readable medium on which program elements are stored that are readable and executable by a computer, in order to perform steps of the inventive method, when the program elements are executed by the computer.

The realization of the disclosure by a computer program a computer program product and/or a computer-readable medium has the advantage that already existing providing systems can be easily adopted by software updates in order to work as proposed by the disclosure.

The computer program product can be, for example, a computer program or comprise another element next to the computer program as such. This other element can be hardware, for example a memory device, on which the computer program is stored, a hardware key for using the computer program and the like, and/or software, for example a documentation or a software key for using the computer program. The computer program product may further comprise development material, a runtime system and/or databases or libraries. The computer program product may be distributed among several computer instances.

The computer program, program code, corresponding instructions or some combination thereof, may also be loaded from a separate computer readable storage medium into the computer using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium.

Figure 1:
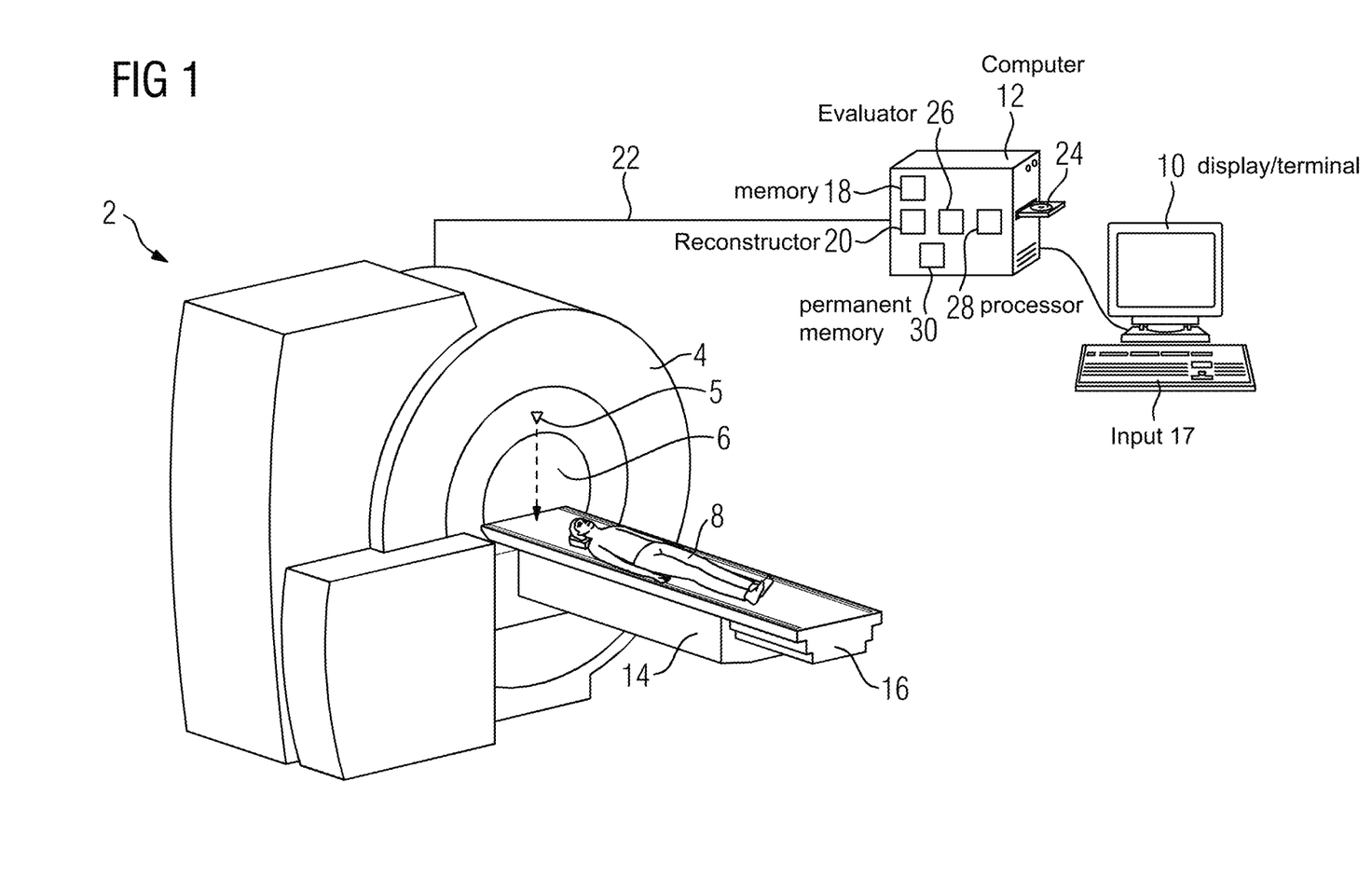
FIG. 1 illustrates a medical imaging system, according to an exemplary embodiment, including a computer.

FIG. 1 depicts a medical imaging system 2 in the form of a magnetic resonance tomograph (magnetic resonance scanner) according to an embodiment of the present disclosure. The magnetic resonance tomograph 2 comprises a hollow cylindrical base 4 in whose interior, what is known as the tunnel 6, an electromagnetic field is generated during operation for a magnetic resonance scan or examination of an examination object in the form of a patient 8. Furthermore, an examination couch 14 having a movable board 16 is provided. The patient 8 can be positioned on the board 16 like illustrated. The examination couch 14 is positioned outside of the base 4 such that the board 16 together with patient 8 can be moved at least partially into the tunnel 6 for the examination. Arranged on the housing of the base 4 above the entrance to the tunnel 6 is a laser marker 5 or a marking laser in the form of a laser source whose laser beam (broken-line arrow) propagates vertically downward onto the examination table 16. The laser marker 5 can be used for defining an isocenter position. The tomograph 2 comprises an arithmetic logic unit in the form of a computer 12 which is designed as a computer and for carrying out at least one embodiment of the inventive method. The computer 12 is connected to a display 10, for example for graphical display of a medical result image, and to an input 17. The display 10 can be for example an LCD, plasma or OLED screen. It can also be a touch-sensitive screen which is also designed as an input 17. A touch-sensitive screen of this kind can be integrated in the imaging device or be designed as part of a mobile and/or portable device. The input 17 is for example a keyboard, a mouse, the mentioned touch screen or even a microphone for speech input. The input 17 may for example be used to manually input a threshold value for a first and/or second parameter.

The computer 12 is also connected to the base 4 of the tomograph 2 for data exchange, especially to a controller of the medical imaging system which is configured to control an image acquisition procedure like e.g. according to a Neuro BOLD fmri protocol. For example, this connection may serve to acquire at least one first parameter corresponding to an imaging protocol parameter. Each imaging protocol is coordinated with a certain type of examination and/or imaging procedure.

The tomograph 2 is adapted for the examination using a selected scanning or imaging protocol, for which examination scan data is acquired for further processing in a reconstructor 20, which in this embodiment is further comprised by the computer 12. A connection for data exchange 22 is implemented wired or wirelessly in a known manner by way of appropriate interfaces. In an exemplary embodiment, the computer 12 (including one or more of its components) includes processor circuitry that is configured to perform one or more operations and/or functions of the computer 12.

The computer 12 also comprises an evaluator 26 which is configured to acquire and evaluate at least one first parameter representative for the medical image acquisition procedure. With other words, the evaluator is configured to process the at least one first parameter to determine, if the plurality of single-frame images is permanently stored prior to assembling at least parts of them into a multi-frame image. Preferably, the evaluator is provided with and/or has access to the at least one first parameter and respective threshold values. Thus, the evaluator has corresponding interfaces to correspond with either the base 4 and or the storage device (memory) 18 of the computer 12.

The computer 12 further comprises a temporal storage and processor 28 configured to temporarily store the plurality of single-frame images and to combine at least partially the plurality of single-frame images to generate the at least one result image. With other words, the temporal storage and processor 28 has access to the plurality of single-frame images received e.g. via a data connection interface from the base 4. Preferably, the temporal storage and processor 28 is configured to transfer or write at least partially the plurality of single-frame images into one coherent multi-frame image, preferably according to DICOM format. A DICOM multi-frame image comprises a header part containing meta-information related or applicable to all imaging information contained in the multi-frame image. In an exemplary embodiment, the temporal storage and processor 28 is located closely to the medical imaging system 2. In an exemplary embodiment, temporal storage and processor 28 is physically integrated into the medical imaging system 2.

The temporal storage and processor 28 may be implemented as working memory, e.g. as a random access memory (RAM), e.g. a statistical RAM, a dynamic RAM or the like.

The computer 12 further comprises a permanent memory storage unit (permanent memory) 30 configured to permanently store either the plurality of single-frame images according to the store-first approach and/or the at least one result image according to the process-first approach. Of course, also the store-first approach comprises permanently storing the result image upon its generation. With other words, the store-first approach comprises storing the plurality of the single-frame images and the at least one result image in the permanent memory storage unit 30.

Accordingly, the storage unit 30 communicates at least with the temporal storage and processor 28 and/or with the reconstructor 20 to acquire the plurality of single-frame images and/or the result image via a corresponding interface.

The permanent memory storage unit 30 may be implemented as a PACS system, or any kind of image storage system or server, which may likewise be located in the cloud.

In the present embodiment, the recontructor 20, evaluator 26, temporal storage and processor 28 and permanent memory storage unit 30 are designed as separate modules within the computer 12, which, where necessary, can exchange data with each other. Alternatively, the recontructor 20, evaluator 26, temporal storage and processor 28 and permanent memory storage unit 30 can be integrated as an arithmetic logic unit, be it in the form of physical or functional integrity.

The computer 12 can interact with a computer-readable data carrier 24, in particular in order to carry out an embodiment of an inventive method by a computer program having program code. Furthermore, the computer program can be retrievably stored on the machine-readable carrier. In particular, the machine-readable carrier 24 can be a CD, DVD, Blu-Ray disk, a memory stick or a hard disk.

The evaluator 26, temporal storage and processor 28 and permanent memory storage unit 30 may be designed in the form of hardware or in the form of software. In an exemplary embodiment, the recontructor 20, evaluator 26, temporal storage and processor 28 and permanent memory storage unit 30 are designed as FPGAs ("Field Programmable Gate Array") or include an arithmetic logic unit.

At least one computer program can be stored on the storage device 18 of the computer 12, and this carries out all method steps of an embodiment of the inventive method when the computer program is run on the computer. The computer program for carrying out the method steps of an embodiment of the inventive method comprises program code. Furthermore, the computer program can be configured as an executable file and/or be stored on a different computing system from the computer 12. For example, the magnetic resonance tomograph (magnetic resonance scanner) 2 can be designed such that the computer 12 loads the computer program for carrying out an embodiment of the inventive method via an Intranet or the Internet into its internal working memory. Alternatively, it can be provided that the computer 12 itself is part of an Internet or Intranet, for example a HIS (Hospital Information System) or a RIS (Radiology Information System) and has access to input, selected or centrally stored scanning protocols of various magnetic resonance tomographs 2 of the facility in order to carry out the inventive method centrally for various tomographs 2.

Generally, medical images may be reconstructed one by one within an imaging data processing pipeline and they can be made sequentially for further assembly into result images in the form of multi-frame DICOM images. There exist two distinctive possibilities how to construct the result images.

According to the 'Store First' approach, the risk of losing image data due to unexpected power disruption or lack of available storage space is minimal. Single-frames images or single frames are permanently stored as soon as they are reconstructed in the image processing pipeline. Only after the last single frame is processed, assembly of the single-frame images into a multi-frame image is done. This approach requires extra time spent on permanently storing and re-reading these single frames before saving them as a result image in multi-frame format. This adds additional processing time and causes a delayed availability of the at least one multi-frame image, i.e. result image. Depending on the relation between the time necessary to save an individual single frame and the time between two consecutive reconstructed single frame images, there exist three different time-dependent functions for the memory occupancy according to below cases case 1, case 2 and case 3. For all cases, a total of three individual single-frame images is assumed. All three example cases are illustrative for typical scenarios, which might be addressed differently according to the present disclosure. However, the present disclosure is not limited to the presented three example cases.

In case 1, time to save a single frame is around 3.5 times longer (e.g. due to very slow storage unit or extremely high frequency of incoming single frames) than the time between two incoming single frames. In this case, single frames stay longer in the storage unit. Total saving time of all single frames is 5.5 times the time between two incoming single frames.

In case 2, saving time is shorter, i.e. only 1.5 times the time between two incoming single frames. Total saving time of all single frames is here about 3.5 times the time between two incoming single frames.

Finally, in case 3, time to save one single frame is quicker than the time between two incoming single frames. This is the most efficient case, as the total saving time is only around 2.5 times the time between two incoming single frames.

The three cases demonstrate the differences as regards memory occupancy for the working memory, i.e. the temporal storage and processor 28, depending on inflow frequency of single frame images from the reconstructor 20 and the time needed to save one single frame. If time to save an individual image is slower, e.g. due to the use of a network drive or a slow internal drive, etc. than the time between two incoming single-frame images, case 1 applies (ratio is 3.5 to 1). In case 2, the ratio is reduced to 1.5 to 1. Finally, case 3 depicts a shorter saving time than inflow time.

Figure 2:
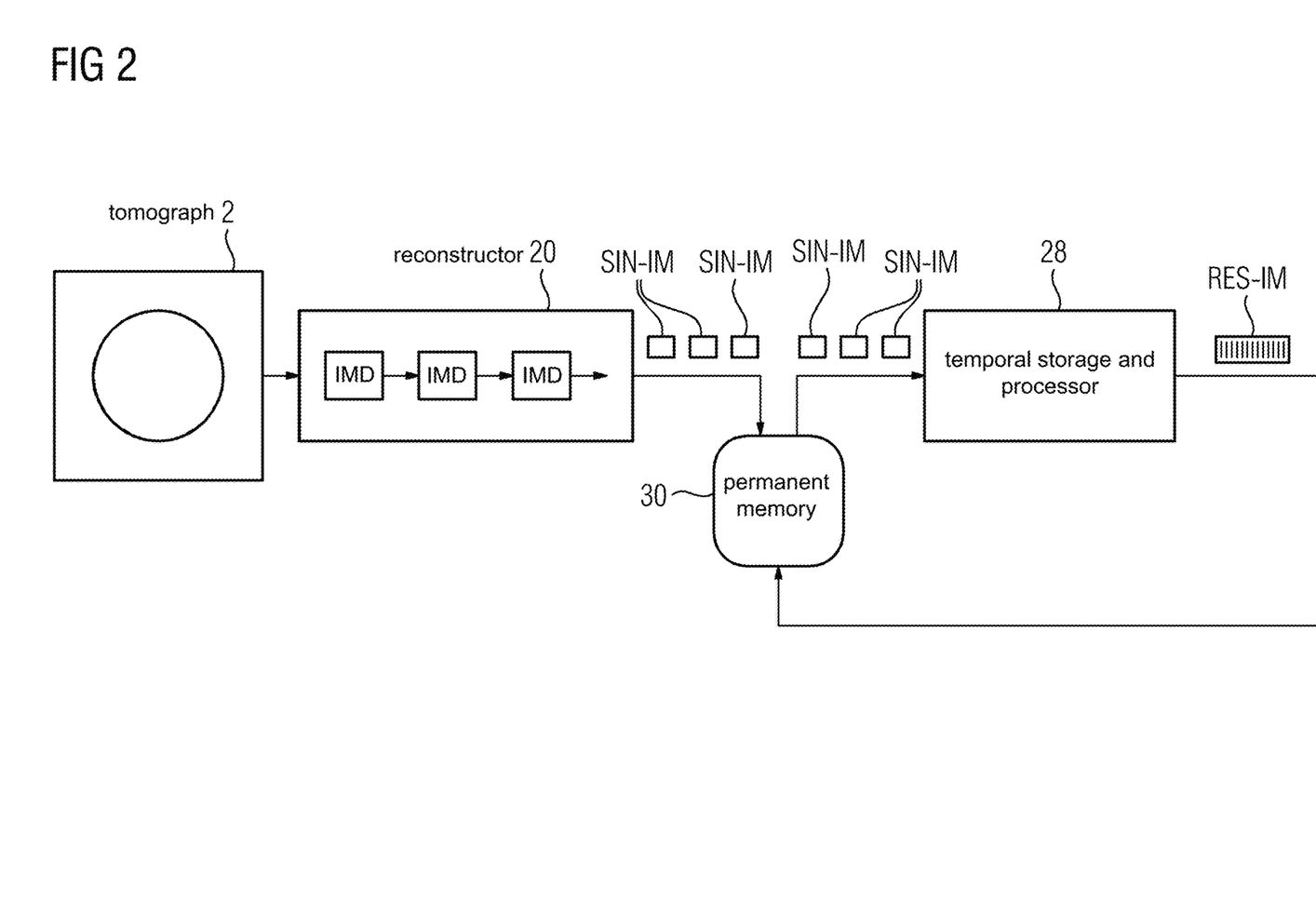
FIG. 2 illustrates a 'Store First' process according to an exemplary embodiment.

FIG. 2 depicts a schematic overview of the inventive method according to the above described 'Store First' approach of the present disclosure.

Here, image measurement data are acquired with the inventive magnetic resonance imaging system 2. The image measurement data are reconstructed by the reconstructor 20 to at least one individual single-frame image SIN-IM. The single-frame images SIN-IM are then output and transferred to the permanent memory storage unit 30 for permanent storage. After permanently storing the single-frames one after the other, the single frames SIN-IM are re-read from the permanent memory storage unit 30 and transferred to the temporal storage and processor 28. The temporal storage and processor 28 assembles at least partially the single-frame images SIN-IM to generate at least one result image RES-IM. The result image RES-IM corresponds to a DICOM multi-frame image comprising at least two, preferably a plurality up to several hundred of single-frame images SIN-IM. The at least one result image RES-IM is then transferred to the permanent memory storage unit 30 for permanent storage.

According to the alternative 'Process First' single-frame images are assembled into a multi-frame image before they are permanently stored. Availability time for the multi-frame image is advantageously small, however the risk of losing image data somewhere within the processing pipeline is increased. Accordingly, this approach assumes that the frames are first assembled and then processed at once before being saved to the permanent memory storage unit. Again, assuming a total of three individual single-frame images, overall time of processing and saving the single frames already combined to a multi-frame image is around 3.8 times the time between two incoming frames.

Figure 3:
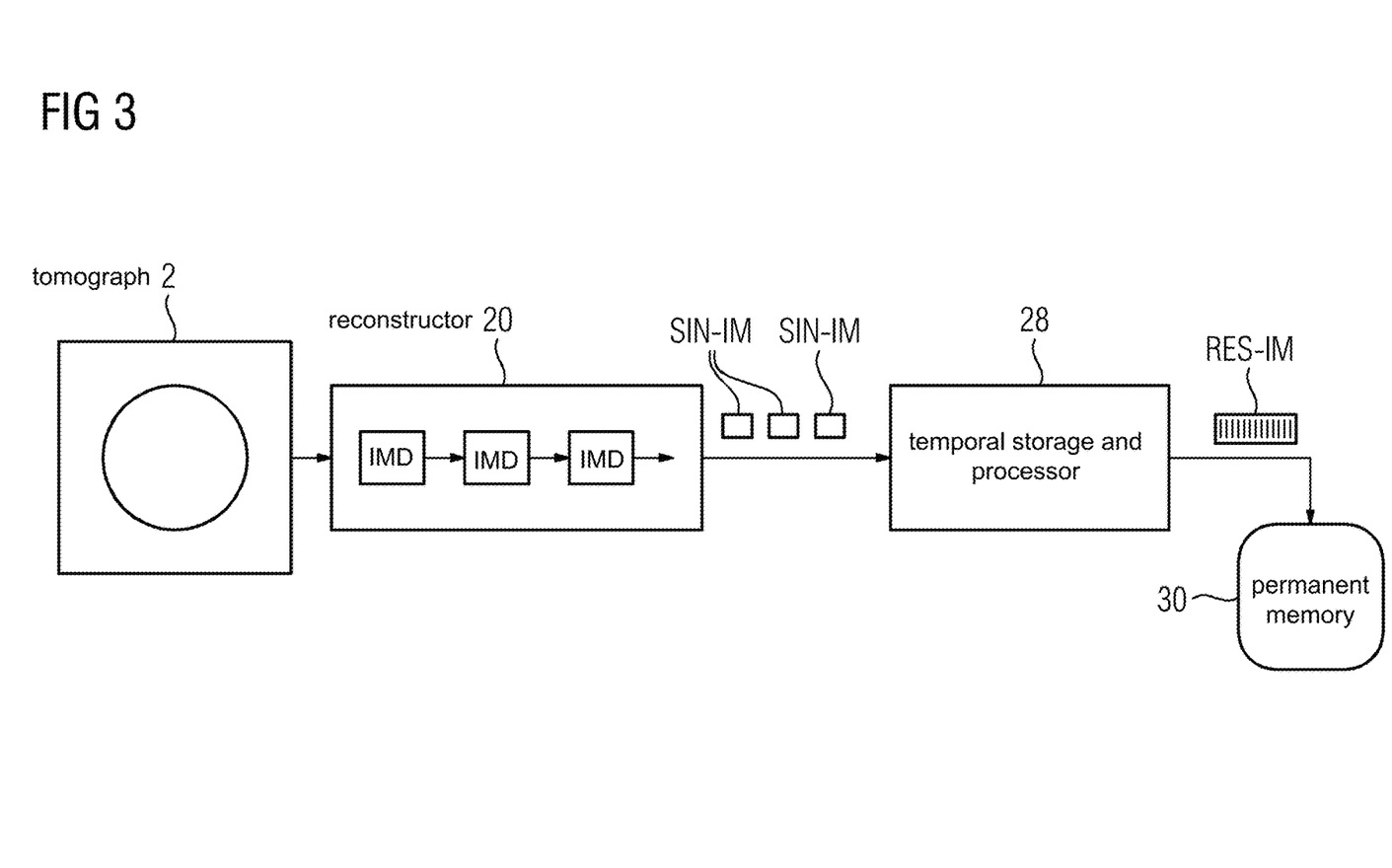
FIG. 3 illustrates a 'Process First' process according to an exemplary embodiment.

FIG. 3 depicts a schematic overview of the inventive method according to the above described 'Process First' approach of the present disclosure.

Here, image measurement data are acquired with the inventive magnetic resonance imaging system 2. The image measurement data are reconstructed by the reconstructor 20 to at least one, preferably a plurality of individual single-frame image SIN-IM. The single-frame images SIN-IM are then output and directly transferred to the temporal storage and processor 28. The temporal storage and processor 28 assembles at least partially the single-frame images SIN-IM to generate at least one result image RES-IM. The result image RES-IM corresponds to a DICOM multi-frame image comprising at least two, preferably a plurality up to several hundred of single-frame images SIN-IM. The at least one result image RES-IM is then transferred to the permanent memory storage unit 30 for permanent storage. With other words, according to this alternative, the single-frame images SIN-IM are not permanently stored one by one.

Time Analysis

In the 'Store First' approach, the time for saving a result image in the form of a DICOM multi-frame image is given as:

$$t_{sf} = \left(n + \frac{t_s}{t_i} - 1\right) * t_i + t_{read} + t_{process} + t_{save}$$

with
n—total number of received single frames
$t_{sf}$—total time to create a DICOM multi-frame image according to 'Store First' approach
$t_s$—time to permanently save one single frame
$t_i$—time between two incoming single frames
$t_{read}$—time to read all permanently saved single frames
$t_{process}$—time to generate a multi-frame image from saved single frames
$t_{save}$—time to save the multi-frame image The time to receive all single frames is defined by the sum of all received single frames and ratio $$\frac{t_s}{t_i},$$

i.e. the ratio between the time to permanently save one single frame and the time between two incoming single frames (reduced by 1). Furthermore, once the single frames are securely stored, they need to be re-read from permanent memory storage unit, processed and saved again. According to above case 1, total saving time for all three single frames is given by $$\left(n + \frac{t_s}{t_i} - 1\right) * t_i = \left(3 + \frac{3.5}{1} - 1\right) * t_i = 5.5 * t_i$$

In the 'Process First' approach, total processing and storing time depends on the total number of received single frames (reduced by 1) and the time needed for processing and permanently saving the constructed multi-frame image by:

$$t_{pf} = (n-1) * t_i + t_{process} + t_{save}$$

with
$t_{pf}$—total time to create a DICOM multi-frame image in according to 'Process First' approach
The remaining variables correspond to the ones already explained with respect to the 'Store First' Approach.

The mutual relationship between these two times can be established as follows:

$$t_{sf} = t_{pf} + t_s + t_{read}$$

Accordingly, the overall 'Store First' time is equal to the overall 'Process First' time with additional time to save one single frame and time to re-read the permanently saved single frames.

Accordingly, the 'Store First' approach needs greater total creation time for a DICOM multi-frame image than the 'Process First' approach, mostly because of re-reading time of the permanently saved single-frame images to process them. On the other hand, as already explained, any disruption in processing (e.g. power loss or lack of available storage space) could result in data loss with the 'Process First' approach.

According to the disclosure, the choice between the two approaches will heavily depend on the imaging procedure. The imaging procedure basically depends on the referring medical question, the initial suspicion, the body region which shall be imaged type of application that is being considered.

Figure 4:
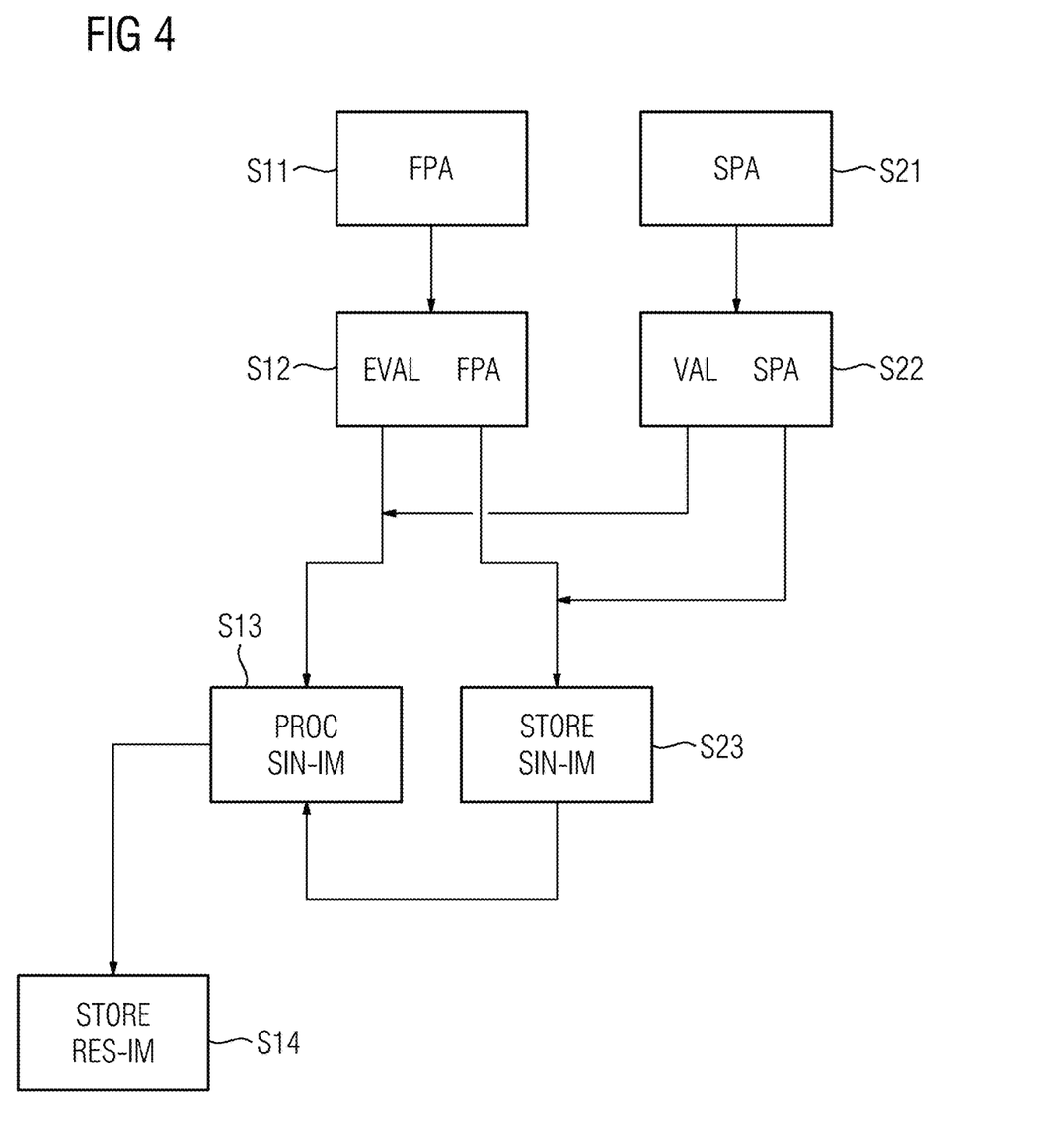
FIG. 4 illustrates a flow chart of a result image generation method according to an exemplary embodiment of the present disclosure.

FIG. 4 depicts a schematic flow chart of the inventive method according to an embodiment of the present disclosure. The inventive method comprises a decision which of both the above described approaches is best suited for generation of a result image.

The following description assumes that a plurality of single-frame images SIN-IM is already acquired and/or reconstructed. The plurality of single-frame images corresponds to at least one volumetric image stack, wherein each of the plurality of single-frame images corresponds to a two-dimensional slice within the at least one volume or to a time series depicting at least one body region according to the imaged field of view at different time points.

According to a first step S11 a first parameter FPA is acquired. The method comprises the acquisition of only one first parameter FPA, preferably however, more than one first parameter FPA is acquired. The at least one first parameter FPA preferably is a protocol parameter. A protocol parameter is characterized in that is defines the imaging protocol applied for the medical image acquisition procedure to generate the plurality of single-frame images SIN-IM.

Preferably, the at least one first parameter FPA is one of the following group of parameters, most preferably more than one:
- the total number of single-frame images SIN-IM acquired for the medical image acquisition procedure,
- total number of result images RES-IM acquired for the medical image acquisition procedure,
- number of single-frame images SIN-IM of one of a result images, i.e. plurality of multi-frame images RES-IM acquired for the medical image acquisition procedure, i.e. the number of single-frames SIN-IM contributing to one result image RES-IM in case, more than one result image is to be generated according to the image acquisition procedure, and
- size of one of at least one of the plurality of single-frame images, i.e. the total number of pixels of one single-frame image SIN-IM or the number of pixels in at least one of the two spatial dimensions or the single-frame image SIN-IM.

All mentioned first parameters may impact alone or on combination the overall storing and processing velocity.

The at least one first parameter may preferably be fetched by the evaluator 26 from the used imaging modality, e.g. the magnetic resonance system 2 according to FIG. 1. Alternatively, the at least one first parameter may be automatically pushed into the internal storage 18 of the inventive computer 12 and retrieved by the evaluator 26.

In a further step S12 the at least one first parameter is evaluated. This evaluation may comprise the comparison of the parameter value with a predefined threshold value. The threshold value may be automatically or manually predefined. Preferably, the threshold value corresponds to or depends on the image acquisition procedure. With other words, depending on the image acquisition procedure the threshold value may differ.

Each of the plurality of first parameters may be evaluated individually. In this case, each first parameter may be compared to its corresponding threshold value. Alternatively, evaluation may comprise to correlate more than one of the first parameters, in case more than one parameter is acquired and considered. In this case, their correlation and/or common impact on the imaging procedure may be evaluated, too. Especially, a plurality of first parameters may have an antagonistic impact on the decision which alternative to apply.

For example, for medical imaging protocols that produce a high volume of imaging data, i.e. a high number of single-frame images SIN-IM, but in relatively small chunks, i.e. many three-dimensional volume images, i.e. result images RES-IM each comprising only a small number of single frames SIN-IM, it is appropriate to apply the 'Process First' approach. In this way, each of the result images RES-IM is available very fast.

For medical protocols that continuously produce a high number of single-frame images SIN-IM without a predefined number of single-frames SIN-IM or result images RES-IM in advance, it is rather impractical to apply the 'Process First' approach. This is due to the fact, that the increasing and unknown number of incoming single frames SIN-IM linearly increases memory consumption of the temporal storage and processor and potentially to its exhaustion leading to danger of losing data. Here, the 'Store First' approach would be appropriate.

According to an optional step S21 at least one second parameter is acquired. This at least one second parameter is indicative or representative of the storage behavior of the temporal storage and processor 28 or the permanent memory storage unit 30. With other words, the at least one second parameter may comprise information on the general performance and/or processing velocity of the storage and processors available. This at least one second parameter may especially influence the decision between the two different approaches in cases, where the performance value for any of the storage units varies with image data load.

The acquisition step S21 is likewise carried out by the evaluator 26. The acquisition may comprise direct communication and (meta) data exchange between the evaluator 26 and either one of the storage and processors 28, 30.

Accordingly, in a further optional step S22 the at least one second parameter is also evaluated. Evaluation is carried out by the evaluator 26.

The evaluation steps S12 and optional S22 provide a result corresponding to a decision between the two approaches 'Process First' and 'Store First'.

According to this evaluation result, the plurality of single-frame images SIN-IM is, according to a first alternative, transferred from the reconstructor 20 to the temporal storage and processor 28, where, according to step S13 of the inventive method, the plurality of single-frame images SIN-IM or at least a sub-group of the plurality of single-frame images SIN-IM is combined into at least one DICOM multi-frame image, which builds the at least one result image RES-IM. This procedure corresponds to the 'Process First' approach. This approach is preferably applied in cases with a small total number of single frame images. The threshold value for this alternative in case, that only this one first parameter is considered is preferably 200.

Alternatively, the plurality of single-frame images SIN-IM is transferred from the reconstructor 20 directly to the permanent memory storage unit 30, where, according to step S23 of the inventive method, the plurality of single-frame images is permanently stored. This procedure corresponds to the 'Store First' approach. This approach is preferably applied in for protocols without a predefined number of single-frame images (so called 'interactive protocols') or with a plurality of result images according to sub-volumes, wherein each result image is comprised of e.g. more than 200 images.

A further alternative approach according to a sub-category of the 'Store First' approach allows the permanent storage of subgroups of the plurality of single-frame images SIN-IM in the permanent memory storage unit 30. The storage of subgroups of single-frame images SIN-IM may comprise storing the subgroups of single-frame images one after the other. As soon as one subgroup of single-frame images is permanently stored, the subgroup is re-read from the permanent memory storage unit 30 and transferred to the temporal storage and processor 28. Re-reading may thus already take place while following subgroups of single-frame images SIN-IM are still in the course of being permanently stored. Such 'Hybrid' approach would take benefit of both the 'Store First' and 'Process First' approaches. For example, according to the 'Hybrid' approach, 10 single-frame images SIN-IM are given an image memory allocation in the permanent memory storage unit 30. After that, the 10 single frames are transferred to the temporal storage and processor 28 and are there concatenated to generate the corresponding result image RES-IM.

Step S23, permanently storing the individual single frames SIN-IM, is followed by step S13, according to which the permanently stored single-frame images SIN-IM are combined or concatenated in the temporal storage and processor 28 to build up a DICOM multi-frame image as a result image RES-IM.

Step 13, according to all alternative approaches, is followed by transferring the at least one result image RES-IM to the permanent memory storage unit 30 and storing the result image RES-IM in the permanent memory storage unit 30, according to the last step S14 of the inventive method.

In the following, application examples are given to better illustrate the inventive method:

Neuro Bold FMRI Protocol

According to this particular protocol, big quantities, e.g. several hundred like 500 to 700, sometimes even more than 1000, medical single frame images are produced, which are organized in small three-dimensional sub-volumes. Each of the sub-volumes typically comprises only a few tens of single frames, e.g. ten to 50, especially 30 to 40, single frames. Here, the inventive decision process could analyze the total number of single-frame images as well as the total number of result images as first parameters. The value for the total number of single-frame images is very high, which would per se lead to a 'Store First' approach. However, the total number of single frame images per result image is very low (as the number of result images is high), the 'Process First' approach is appropriate. This is due to the fact that, since the number of single frame images transferred to the temporal storage and processor 28 is small and the single frames are regularly organized into logical sub-volumes (multi-frame images).

Interactive Real-Time Protocol

This protocol continuously creates single image frames without initially defining the desired image quantity at the end of the measurement. There is no sub-organization of the single frames. Thus, the 'Store First' would be the most effective approach since images are securely saved without exhausting working memory limits. Final timing of availability of all created images after image acquisition is uncritical in this case, as the reconstructed single frame images are immediately displayed in real time, e.g. via the display 10.

Wherever meaningful, individual embodiments or their individual aspects and features can be combined or exchanged with one another without limiting or widening the scope of the present disclosure. Advantages which are described with respect to one embodiment of the present disclosure are, wherever applicable, also advantageous to other embodiments of the present disclosure.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc.

Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for generating at least one medical result image from a plurality of single-frame images associated with a medical image acquisition procedure conducted with a medical imaging system, the method comprising:
receiving an electronic data signal indicative of at least one first parameter representative of the medical image acquisition procedure to acquire the at least one first parameter, the at least one first parameter comprising a protocol parameter characterizing an imaging protocol applied for the medical image acquisition procedure, and is indicative of a total number of medical result images acquired for the medical image acquisition procedure;
evaluating the at least one first parameter to determine an evaluation result, the evaluating including comparing the at least one first parameter to a threshold value, the evaluation result being determined based on the comparison, wherein the threshold value is adaptively adjusted based on the medical image acquisition procedure associated with the at least one first parameter and conducted with the medical imaging system; and
based on the evaluation result, controlling the medical imaging system to selectively operate in a first mode of operation and a second mode of operation to generate the at least one medical result image as a multi-frame image in which redundant meta-information identified with the plurality of single-frame images has been removed, wherein:
when in the first mode of operation, storing the plurality of single-frame images only in a temporary storage and processor unit and combining, at least partially, the temporarily-stored plurality of single-frame images to generate the at least one medical result image before permanently storing the at least one medical result image; and
when in the second mode of operation, permanently storing the plurality of single-frame images in a permanent storage unit before combining the plurality of single-frame images to generate and permanently store the at least one medical result image.

2. The method according to claim 1, wherein permanently storing the plurality of single-frame images before combining the plurality of single-frame images to generate the at least one medical result image comprises:
permanently storing a sub-group of the plurality of single-frame images before combining the sub-group of the plurality of single-frame images to generate the at least one medical result image.

3. The method according to claim 2, wherein, in response to the at least one first parameter being less than the threshold value, operating in the first mode of operation, and wherein the method comprises:
transferring the plurality of single-frame images to the temporary storage and processor unit;
combining the plurality of single-frame images, by the temporary storage and processor unit, to generate the at least one medical result image;
transferring the at least one medical result image to the permanent storage unit; and
permanently storing the at least one medical result image in the permanent storage unit.

4. The method according to claim 3, wherein, in response to the at least one first parameter being greater than the predefined threshold, operating in the second mode of operation, and wherein the method comprises:
transferring the plurality of single-frame images to the permanent storage unit;
permanently storing the plurality of single-frame images in the permanent storage unit;
transferring the plurality of single-frame images to the temporary storage and processor unit;
combining the plurality of single-frame images, by the temporary storage and processor unit, to generate the at least one medical result image;
transferring the at least one medical result image to a permanent storage unit; and
permanently storing the at least one medical result image in the permanent storage unit.

5. The method according to claim 1, wherein, in response to the at least one first parameter being less than the threshold value, operating in the first mode of operation, and wherein the method comprises:
transferring the plurality of single-frame images to the temporary storage and processor unit;
combining the plurality of single-frame images, by the temporary storage and processor unit, to generate the at least one medical result image;
transferring the at least one medical result image to the permanent storage unit; and
permanently storing the at least one medical result image in the permanent storage unit.

6. The method according to claim 1, wherein:
in response to the at least one first parameter being less than the threshold value, operating in the first mode of operation, and wherein the method comprises:
transferring the plurality of single-frame images to the temporary storage and processor unit;
combining the plurality of single-frame images, by the temporary storage and processor unit, to generate the at least one medical result image;
transferring the at least one medical result image to the permanent storage unit; and
permanently storing the at least one medical result image in the permanent storage unit; and in response to the at least one first parameter being greater than the threshold value, operating in the second mode of operation, and wherein the method comprises:
transferring the plurality of single-frame images to the permanent storage unit;
permanently storing the plurality of single-frame images in the permanent storage unit;
transferring the plurality of single-frame images to the temporary storage and processor unit;
combining the plurality of single-frame images, by the temporary storage and processor unit, to generate the at least one medical result image;
transferring the at least one medical result image to a permanent storage unit; and
permanently storing the at least one medical result image in the permanent storage unit.

7. The method according to claim 1, further comprising: acquiring a plurality of first parameters; and
evaluating the plurality of first parameters to determine the evaluation result.

8. The method according to claim 1, wherein the at least one first parameter further comprises one of more of:
a total number of single-frame images acquired for the medical image acquisition procedure;
a number of single-frame images of one of a plurality of result images acquired for the medical image acquisition procedure; and/or
a size of one of at least one of the plurality of single-frame images.

9. The method according to claim 1, further comprising: acquiring at least one second parameter and evaluating the at least one second parameter, wherein the at least one second parameter is indicative of a storage behavior of:
the temporary memory configured to temporarily store the plurality of single-frame images; and/or
the permanent storage unit configured to permanently store the plurality of single-frame images.

10. The method according to claim 9, wherein the storage behavior is a performance and/or storage speed of the temporary memory and/or permanent storage unit.

11. A non-transitory computer-readable storage medium with an executable program stored thereon, that when executed, instructs a processor to perform the method of claim 1.

12. A non-transitory computer program product having a computer program which is directly loadable into a memory of the medical imaging system, when executed by a controller of the medical imaging system, causes the medical imaging system to perform the method as claimed in claim 1.

13. The method according to claim 1, further comprising: acquiring a plurality of first parameters;
comparing each first parameter of the plurality of first parameters to a respective threshold value to determine respective evaluation results,
wherein the evaluation result is determined based on the respective evaluation results.

14. The method according to claim 1, wherein the at least one first parameter defines an imaging protocol applied for the medical image acquisition procedure.

15. The method according to claim 1, further comprising: acquiring a plurality of first parameters; and
correlating the plurality of first parameters to determine a correlated parameter, wherein the correlated parameter is compared to the threshold value to determine the evaluation result.

16. The method according to claim 1, wherein the redundant meta-information identified with the plurality of single-frame images comprises one or more of header data referring to a patient, imaging protocol specific data, a patient name, a patient age, and/or the imaging protocol applied for the medical image acquisition procedure.

17. The method according to claim 1, wherein the at least one first parameter is from among a plurality of first parameters, and wherein the act of evaluating the at least one first parameter comprises individually evaluating each one of the plurality of parameters without considering other ones of the plurality of first parameters to determine the evaluation result.

18. A computer configured to generate at least one medical result image from a plurality of single-frame images associated with a medical image acquisition procedure conducted with an imaging system, the computer comprising:
an evaluator configured to: receive an electronic data signal indicative of at least one first parameter representative of the medical image acquisition procedure, the at least one first parameter comprising a protocol parameter characterizing an imaging protocol applied for the medical image acquisition procedure, and is indicative of a total number of medical result images acquired for the medical image acquisition procedure; evaluate the at least one first parameter to determine an evaluation result, and control the computer to selectively operate, based on the evaluation result, in a first mode of operation and a second mode of operation to generate the at least one medical result image as a multi-frame image in which redundant meta-information identified with the plurality of single-frame images has been removed, the evaluating including comparing the at least one first parameter to a threshold value, the evaluation result being determined based on the comparison, wherein the threshold value is adaptively adjusted based on the medical image acquisition procedure associated with the at least one first parameter and conducted with the medical imaging system;
a temporary storage and processor unit configured to: in the first mode of operation, temporarily store the plurality of single-frame images and combine, at least partially, the temporarily-stored plurality of single-frame images to generate the at least one medical result image; and
a permanent storage unit configured to permanently store the generated at least one medical result image, and, in the second mode of operation, permanently store the plurality of single-frame images before the plurality of single-frame images are combined to generate the at least one medical result image.

19. A medical imaging system configured to generate the at least one medical result image from the plurality of single-frame images, the plurality of single-frame images referring to the medical image acquisition procedure conducted with the medical imaging system, the medical imaging system comprising:
a medical imaging scanner configured to acquire image data from a subject, the plurality of single-frame images being based on the acquired image data; and
the computer according to claim 18.

20. The medical imaging system according to claim 19, wherein the medical imaging system is a magnetic resonance imaging system.

* * * * *